United States Patent [19]

Weber, Jr. et al.

[11] Patent Number: 5,408,577
[45] Date of Patent: Apr. 18, 1995

[54] METHOD AND HEATER APPARATUS WITH PROTECTIVE FUSE FOR MEDICAL APPLICATIONS

[75] Inventors: Jaroy Weber, Jr., Woodside; Kenneth C. Kitlas, Fremont, both of Calif.

[73] Assignee: Sonne Medical, Menlo Park, Calif.

[21] Appl. No.: 24,187

[22] Filed: Feb. 26, 1993

Related U.S. Application Data

[63] Continuation-in-part of Ser. No. 852,021, Mar. 16, 1992.

[51] Int. Cl.⁶ .............................. F24H 1/10; H05B 3/58
[52] U.S. Cl. ................................... 392/480; 392/479; 392/484; 219/535; 219/544
[58] Field of Search .................. 392/479, 480–482, 392/484; 219/497, 506, 505, 499, 535, 544

[56] References Cited

U.S. PATENT DOCUMENTS

| | | | |
|---|---|---|---|
| 1,110,919 | 9/1914 | Gamble . | |
| 2,087,586 | 7/1937 | Tishman | 219/39 |
| 3,789,190 | 1/1974 | Orosy et al. | 219/497 |
| 3,803,386 | 4/1974 | Rodriques | 219/523 |
| 3,887,788 | 6/1975 | Seibel et al. | 219/219 |
| 3,890,486 | 6/1975 | Fitzgerald | 219/523 |
| 4,086,466 | 4/1978 | Scharlack | 219/494 |
| 4,256,950 | 3/1981 | Wildgruber | 219/306 |
| 4,314,143 | 2/1982 | Bilstad et al. | 219/497 |
| 4,429,213 | 1/1984 | Mathieu | 219/301 |
| 4,501,956 | 2/1985 | Bergersen et al. | 219/553 |
| 4,549,073 | 10/1985 | Tamura et al. | 219/497 |
| 4,642,155 | 2/1987 | Ramsey | 156/359 |
| 4,847,470 | 7/1989 | Bakke | 219/299 |
| 4,994,655 | 2/1991 | Handa et al. | 219/535 |
| 5,014,210 | 5/1991 | Postlewait et al. | 364/477 |
| 5,089,687 | 2/1992 | Bartrug et al. | 219/203 |
| 5,120,936 | 6/1992 | Shyu et al. | 219/497 |
| 5,170,042 | 12/1992 | Bunn | 219/497 |

*Primary Examiner*—Mark H. Paschall
*Attorney, Agent, or Firm*—Albert C. Smith

[57] ABSTRACT

An inexpensive, disposable heating element is prepared for medical applications using layers of biologically-compatible materials disposed about a heating element that is formed of an electrically conductive material which exhibits positive temperature coefficient of resistance and that is then operated by a power controller which responds to the resistance of the heating element or to other electrical indication of operating temperature in order to control the level of power supplied to the heating element. A fuse is distributed about the periphery of the heating element to disconnect electrical power from the heating element in response to excessive heating of the element attributable to a portion of the heating element, usually including the periphery, not being immersed in liquid being warmed. A connector to the heating element may include a tab that retains coded manifestations thereon of a measured parameter of the heating element, which manifestations may then be detected upon insertion of the connector into a receptacle of a power controller to provide programming signals that set the operating parameters within which the power controller operates the heating element. A flow controller may be disposed adjacent a surface or surfaces of a heating element to confine the flow of a liquid in a selected pattern over the surface or surfaces of the heating element.

4 Claims, 9 Drawing Sheets

METHOD AND HEATER APPARATUS WITH PROTECTIVE FUSE FOR MEDICAL APPLICATIONS

RELATED CASES

This application is a continuation-in-part application of pending application Ser. No. 07/852,021, filed Mar. 16, 1992, pending, entitled "HEATER APPARATUS AND METHOD FOR MEDICAL APPLICATIONS", and the subject matter of this application is related to the subject matter of pending application Ser. No. 07/715,500, now abandoned, entitled "WARMING APPARATUS FOR MEDICAL APPLICATIONS", and to the subject matter disclosed in U.S. Pat. No. 4,967,061.

BACKGROUND OF THE INVENTION

This invention relates to apparatus for warming fluids for medical applications, and more particularly to apparatus for immersion in a fluid to be warmed that is selectively powered and sensed to assure fail-safe operation in and out of the fluid to be warmed.

Many medical procedures require warming fluids in a sterile environment at elevated temperatures that are closely regulated within a narrow range of temperatures. In addition, inexpensive, pre-sterilized, disposable equipment greatly facilitates preparation and clean-up procedures associates with a surgical procedure, and promotes the preservation of sterile conditions from patient to patient.

Electrically-controlled heaters for warming liquids or gases associated with surgical procedures have attained wide acceptance but commonly must be sterilized prior to re-use. Disposable heater units obviate the need for re-sterilization between uses, but inexpensive, single-application heaters to date have not included sufficiently high quality workmanship, materials and designs to assure reliable operation throughout an entire surgical operation. For example, safety features such as thermal cutoff switches typically do not operate satisfactorily if only a portion of an immersed heater remains in contact with a liquid to be warmed. Also, mass production techniques commonly associated with inexpensive, disposable heaters typically are incapable of maintaining close tolerances of electrical parameters to assure repeatable performance from a population of heaters operated in a given surgical application. Such variations in electrical parameters usually contribute to difficulties in controlling the operating temperature within close tolerances.

SUMMARY OF THE INVENTION

In accordance with the present invention, inexpensive, immersible electrical heaters are mass produced with relatively low-tolerance resistance parameters including heater conductors formed of materials that exhibit positive or negative temperature coefficients of resistance. Added costs and complexities of using thermistors as heat sensors in a power controller are eliminated by using the heater conductors to sense the operating temperature. The resistance of the heater conductors is sensed during intervals of no applied power as an indication of the operating temperature in a manner that is suitable for servo controlling the supplied power. The heaters may be individually tested to determine resistance at a selected testing temperature, and may be coded with the test value of resistance in a manner that can be sensed by an electrical power controller to accurately and repeatably power each heater in a population of heaters to selected operating temperatures within close tolerances despite wide variations in resistance values from heater to heater in the population of heaters. In addition, the coding scheme on each heater facilitates automatic programming of numerous selected operating parameters of the heaters and controller. Alternatively, a thermal sensor such as a thermistor may be incorporated into the immersible electrical heater to provide electrical indication of the operating temperature of the heater, and a thermally-sensitive fuse element may be distributed about the heater to disconnect the heater element from a source of applied electrical power in response to a portion of the heater element not submerged in a liquid tending to operate at excessive temperatures.

DESCRIPTION OF THE PREFERRED EMBODIMENT

Figure 1A:
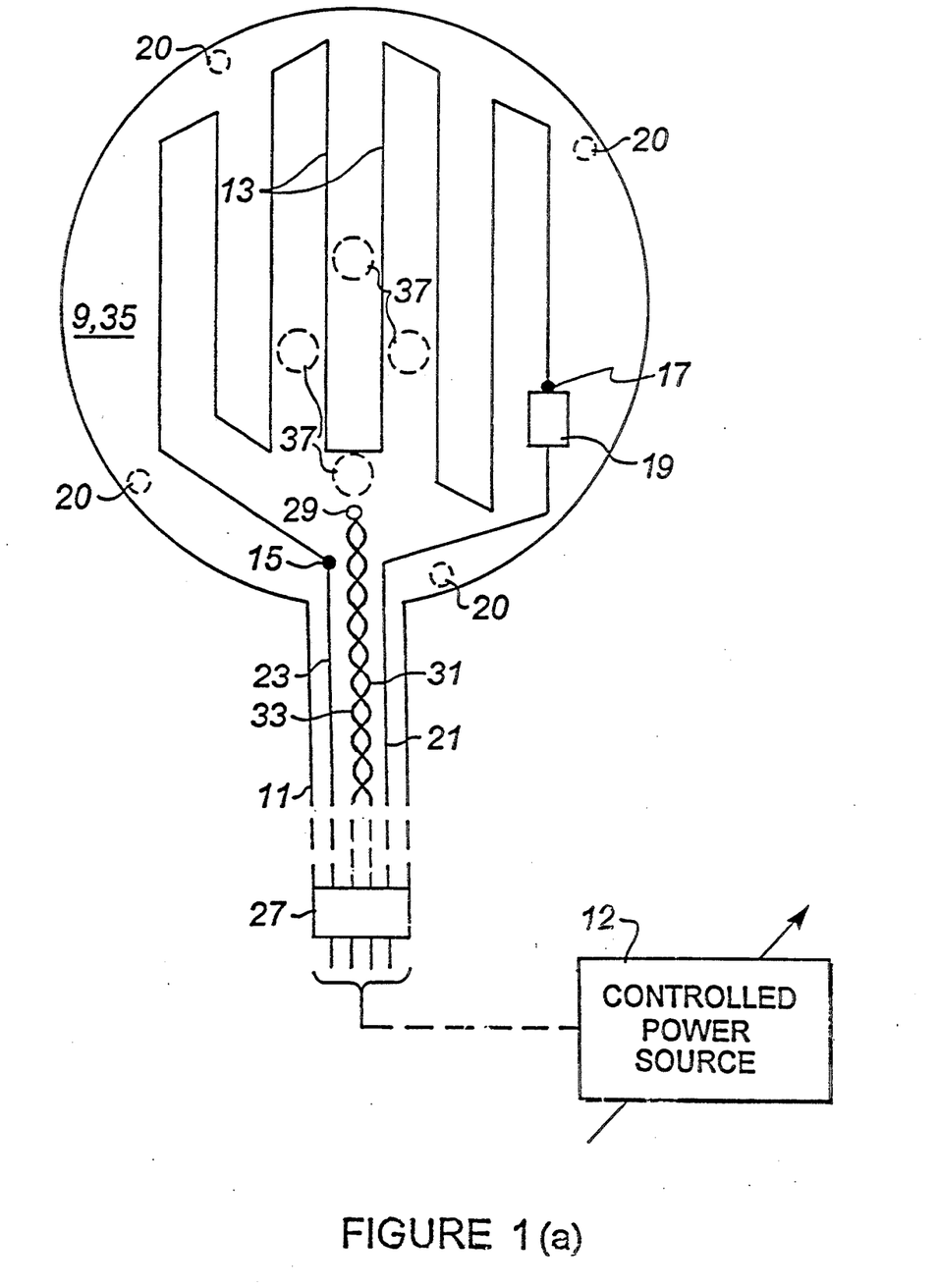
FIG. 1(a) is a plan view of the heater apparatus according to one embodiment of the present invention.

Referring now to FIG. 1(a), there is shown a plan view of an immersible heater according to one embodiment of the present invention. The heater comprises a supporting layer 9 of a biocompatible, electrically-insulating material such as polyvinyl chloride or silicone rubber, generally shaped as a flat disk with a round or other suitable peripheral shape which may include an integrally formed elongated tab 11. Heater element 13 is formed theron of a material having positive (or negative) temperature coefficient of resistance such as, for example, nickel-chromium alloy, or the like, in generally serpentine, continuous pattern between connections or terminals 15, 17. The terminals 15, 17 are connected via a thermal fuse 19 and the conductors 21, 23 which form a cable, or which may be disposed along the elongated tabs 11, to a connector 25 for detachable connection to a controlled source 12 of electrical power that regulates the power supplied to the heater 13 in the manner as later described herein. A thermally-sensitive detector 29 such as a thermistor or thermocouple is also disposed on the disk 9 to provide an electrical indication of the operating temperature of the heater 13. An encapsulating layer 35 of similar biocompatible material is then formed over the supporting layer 9 and fuse 19 and detector 29 to seal in the heater 13 and all associated conductors and terminals against contact with the ambient environment during sterilization or use in warming fluids. The entire sealed structure is ideally relatively flexible and may include one or more apertures 37 therethrough to promote liquid circulation around and through the structure. The detector 29 may be located in proximity to one of the apertures 37 to provide response that is more accurately representative of liquid passing through aperture 37. Flexibility of the sealed structure facilitates conforming of the heater to the shape of a confining vessel, and may facilitate extension of the elongated tab 11 (or connecting cable 11, as illustrated in FIG. 2) out over the rim of a vessel that contains a volume of liquid which is to be warmed by electrical power dissipated in the heater 13.

Figure 1B:
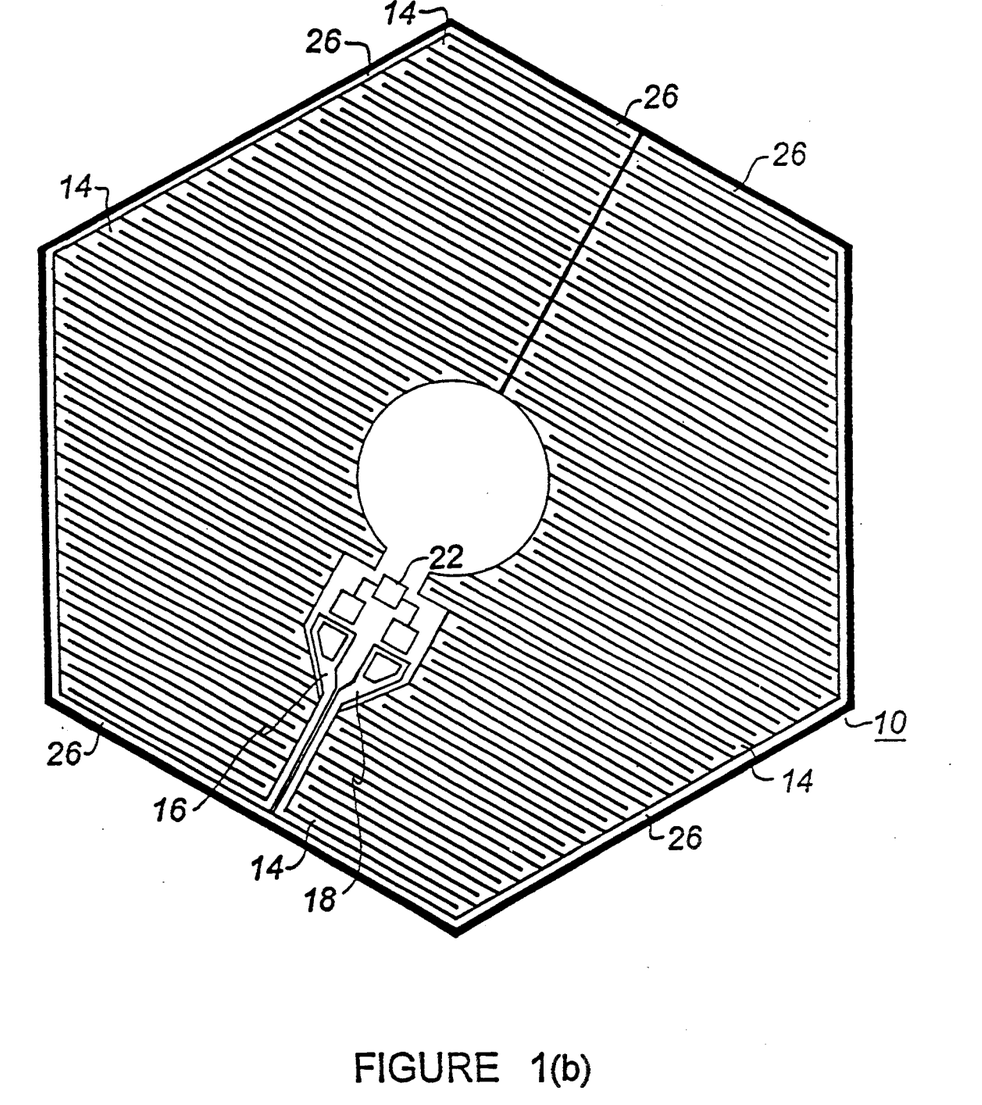
FIG. 1(b) is a plan view of the heater apparatus according to another embodiment of the present invention.

Referring now to FIG. 1(b), there is shown a plan view of another embodiment of the heater apparatus of the present invention. In this embodiment, the heater includes a supporting layer 10 of a biocompatible, electrically-insulating layer of material such as polyvinyl chloride or silicone rubber, or the like, generally shaped as a flat disk with a hexagonal or other suitable peripheral shape. Hexagonal or similar non-round peripheral shape promotes circulation of warmed liquid from below the apparatus within a typically round confirming vessel. Heater element 14 is formed on the layer 10 of a material having a positive or negative temperature coefficient of resistance such as, for example, nickel-chromium alloy, aluminum, or the like, in generally serpentine, continuous pattern within half sectors between terminals 16, 18. A thermally-sensitive trace 26 of the heater element 14 may be disposed substantially about the periphery of layer 10 and may be serially connected with the heater conductors 14 in the half sectors to form a continuous conductor between terminals 16, 18. The fuse formed by trace 26 may thus respond to excessive heating under operating conditions associated with a portion of the apparatus, usually including a peripheral portion, not being immersed in liquid being warmed. In these operating conditions, electrical power supplied to the heater element 14 would heat the portions of the element 14 not being cooled by liquid to sufficiently elevated temperatures to decompose the materials of the present apparatus and thereby contaminate the liquid being heated, and increase the risk of fire in close proximity with surgical drapes and other flammable materials. The peripheral trace 26 may, for example, be fabricated of aluminum that is conventionally sputtered onto the layer 10, or that is etched from aluminum foil attached to the layer 10, or the like, to provide a fuse element that is distributed over an area of the heater apparatus that preferably includes the areas adjacent the periphery. The heater element 14 may be formed, for example, at the same time of the same material as the peripheral trace 26, with the peripheral trace 26 having a smaller cross sectional area, for example, by narrower line width and same thickness to promote higher current density of electrical signal conducted by the peripheral trace 26 than by the heater conductors 14 disposed elsewhere over the surface of the layer 10. In this manner, higher probability of conductor failure, or burn-out, is predicted in the peripheral trace 26 than in the heater conductor 14 elsewhere on the surface of the layer 10, particularly under operating conditions of a portion of the heater apparatus, usually including some peripheral portion, not being immersed in liquid to be heated. Thus, the peripheral trace 26 forms a distributed fuse serially connected with the heater conductor 14 between terminals 16, 18. The central region of the layer 10 may be removed to provide an aperture therethrough to facilitate passage of tubes through the heater apparatus, or to provide the circulation therethrough of liquid to be heated. A thermal detector 22 such as a thermistor or thermocouple may be mounted on the layer 10 near the central region thereof to provide an electrical indication of the operating temperature for power controlling purposes, and a cable of multiple conductors is electrically connected to the detector 22 and terminals 14, 16 for controlling and powering the heater apparatus from a source 12 of electrical power. A second layer of biocompatible material (not shown to preserve clarity) is then disposed over the heater element 14 and distributed fuse 26 and thermal detector 22 and sealed to the first layer and to the cable in conventional manner to encapsulate the heater apparatus and associated terminals and connections against contact with the ambient environment during sterilization or use in warming fluids.

Figure 2:
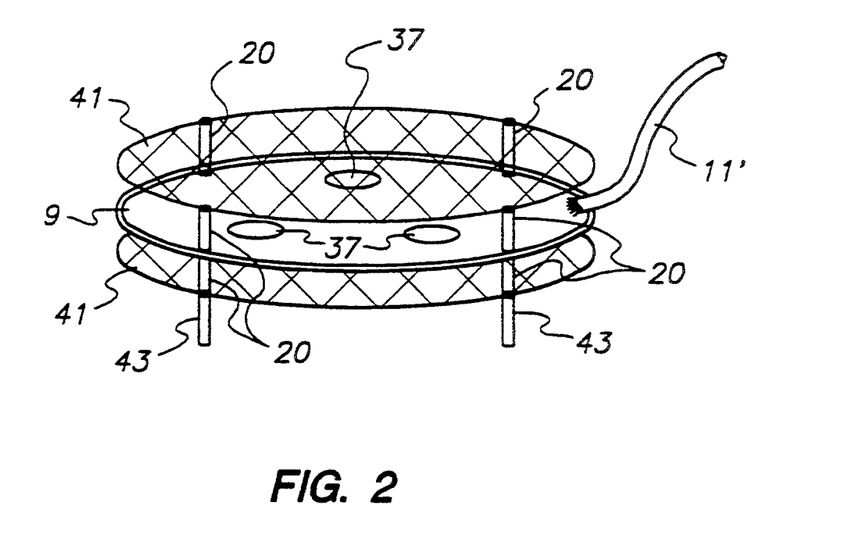
FIG. 2 is a perspective drawing of the heater apparatus according to FIG. 1 positioned within protective frames.

Referring now to FIG. 2 there is shown a perspective view of the heater according to FIG. 2 disposed between a pair of cages or frames 41 that are oriented in spaced relationship to the upper and lower surfaces of a heater 9 or 10. These cages or frames 41 are mounted in the spaced relationship from the heater 9 or 10 by spacers 20 positioned near the perimeter of the heater 9 or 10, and an additional set of 'feet' or spacers 43 may be oriented about the perimeter of the lower cage or frame 41 to support the assembly above a supporting surface (say, the bottom of a basin). The connecting cable 11' of conductors 21 and 23 for the heater element 13 or 14 may be sealed to the heater 9 or 10 and may be sufficiently flexible to permit the convenient routing thereof over the rim of a basin.

Figure 3A:
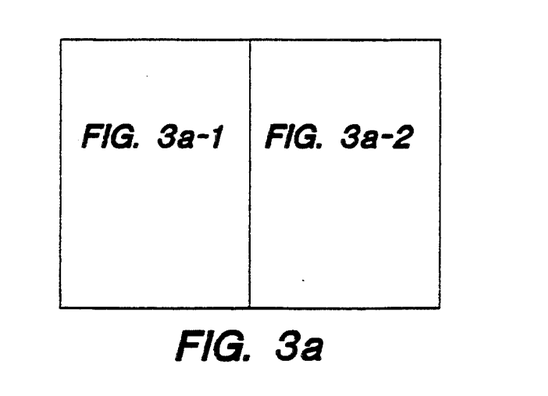
FIG. 3(a) is a schematic diagram of one embodiment of a power controller for the heater apparatus of FIGS. 1 or 2.
Figure 3A:
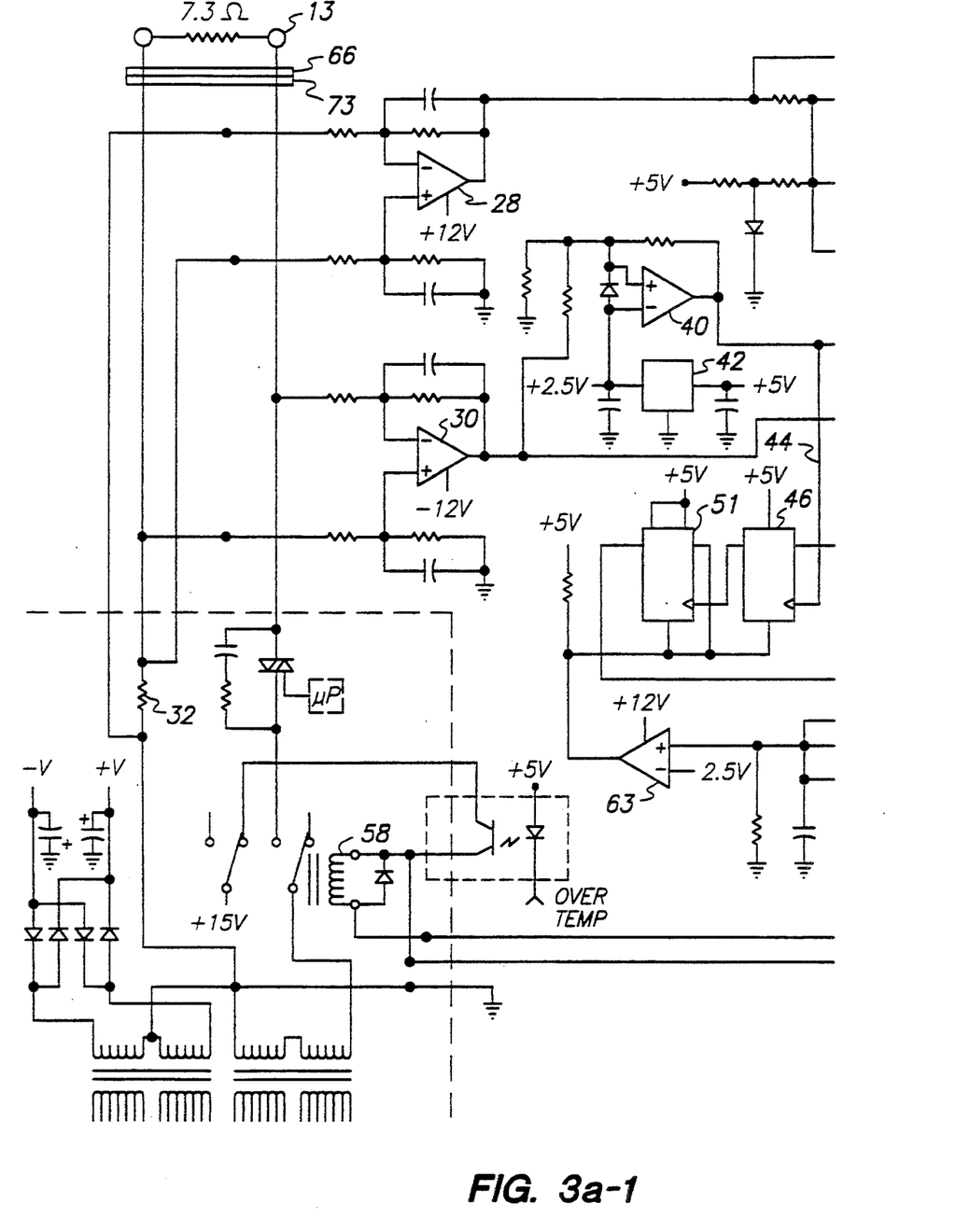
FIG. 3(b) is a graph illustrating the operation of the circuit of FIG. 3(a) during half cycles of power line signal.
Figure 3A:
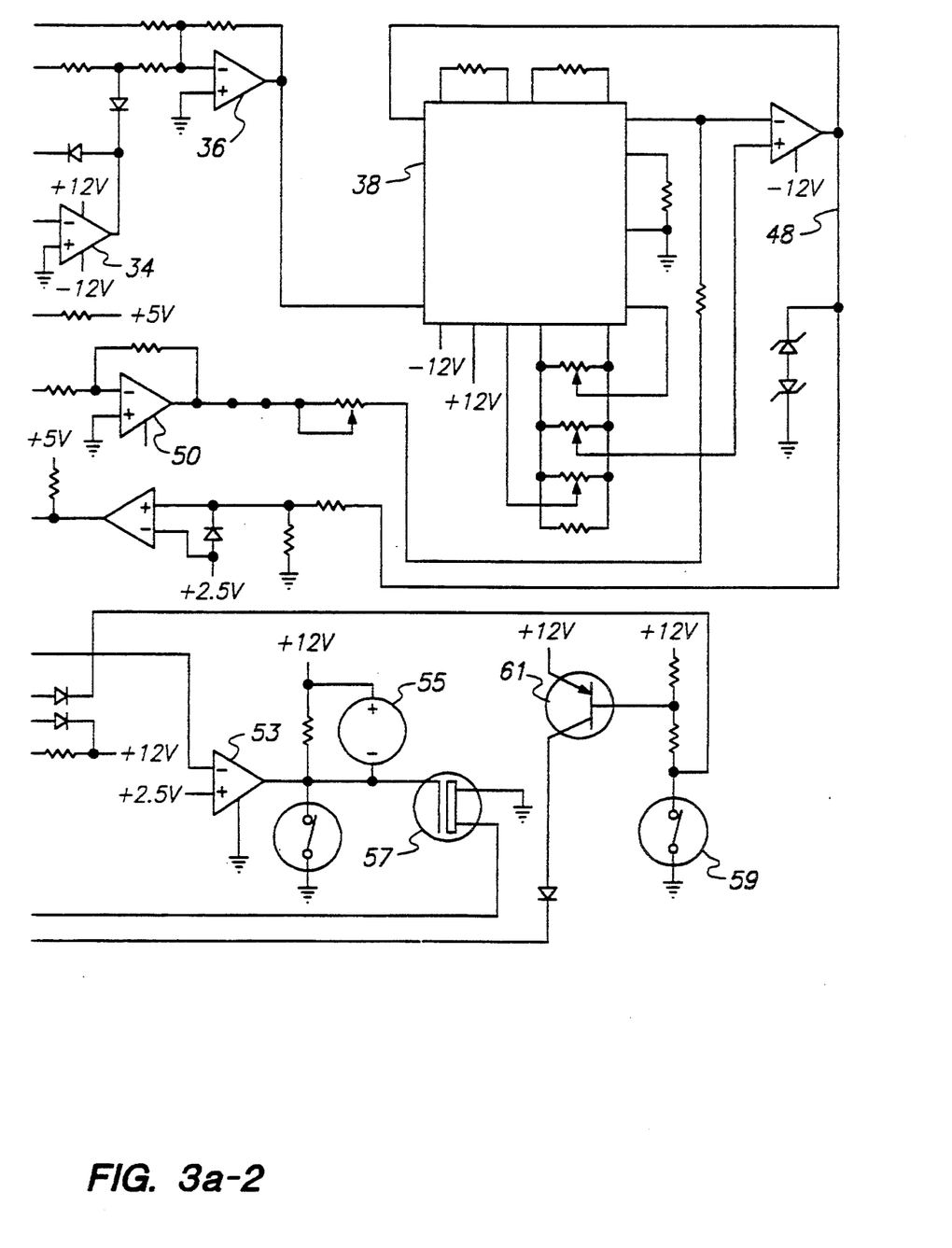
Figure 3B:
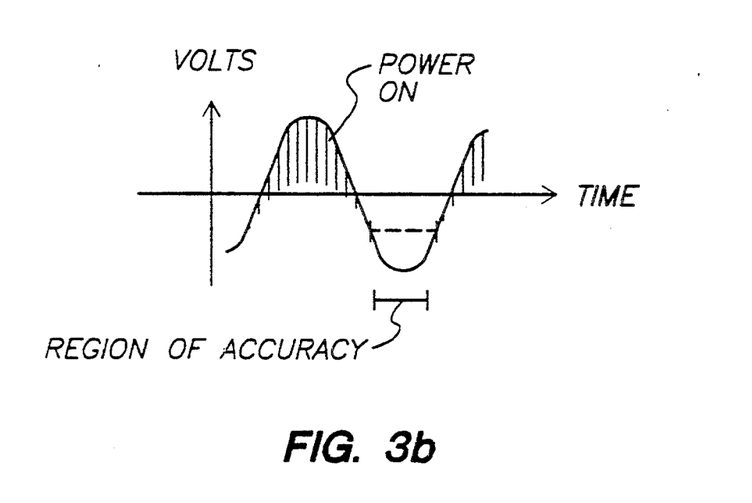

Referring now to FIG. 3(a), there is shown a schematic diagram of one embodiment of a power controller according to the present invention which measures the resistance of the heater 13 or 14 during intervals in which power is not applied to the heater to assure fail safe operation within changing operating conditions. The material that forms the heater has a selected positive or negative temperature coefficient (TC) of resistance and therefore has a certain range of resistances over an operating range of temperatures, say, 15° C. to 43° C. for medical applications, that can be sensed to provide indication (via correlation through the TC) of the temperature of the heater 13 or 14. The resistance thus sensed may be supplied to the power controller as temperature feedback information for closed-loop servo control of applied power, or for safety shutdown control against thermal runaway. The normal operating temperatures are less than the damage thresholds of the heater 13 or 14 and surrounding materials, but injury or damage may occur at elevated temperatures in excess of this temperature range due, for example, to a portion of the heater apparatus being out of contact with a liquid being warmed while the heater 13 or 14 is being powered. Thus, in FIG. 3(*a*), amplifiers 28 and 30 are connected to operate as a differential amplifier. The input to amplifier section 28 is the voltage drop across reference resister 32, and the input to amplifier section 30 is the voltage drop across the heater 13 or 14. The following amplifier section 34, 36 operate on the output of amplifier section 28 as a precision limiter to assure that the resultant output representing current through the heater 13, 14 (as a denominator in the following divider circuit 38) cannot become zero (or, in practice, less than 0.7 volts positive). The voltage signal from amplifier section 30 is applied to the divider circuit 38 as the numerator, and the current signal from amplifier section 28 is applied to the divider circuit 38 as the denominator. Of course, digital division under control of a microprocessor according to conventional technology may also be used in place of divider circuit 38. Voltage comparator 40 and reference voltage source 42 senses a rise in the voltage applied across the heater 13 and 14 to produce an output pulse 44 when the heater voltage exceeds, say 37.5 volts. This output pulse triggers latch 46 that senses whether the output. 48 of the divider 38 is representative of a heater resistance above or below a selected value, say 9 ohms, for a heater of positive TC and initial value that tested at room temperature to be, for example, about 7.3 ohms. The resistance value represented at the output 48 of the divider is not constant over time, and provides only inaccurate resistance indication during one-polarity half cycle of the power-line sine wave and near the zero crossings of the sine wave, as illustrated in the graph of FIG. 3(*b*). The output of amplifier 40 thus establishes time marks of a period within the opposite polarity half of the sine wave during which the resistance of the heater 13, 14 can be sampled accurately for comparison with an upper-limit value to control the shut off of applied power, or to provide servo feedback information for the proportional or direct control of applied power. If the resistance of the heater is sensed to be above the upper limit of, say, 9 ohms, then the Q output of latch 46 goes high to set latch 51. Amplifier 53 senses the Q output of latch 51 which turns on an alarm indicator 55 and turns off power transistor 57 which, in turn, releases relay 58 that turns off power supplied to the heater 13, 14. The upper limit of allowable heater resistance may be exceeded when, for example, a portion of the heater apparatus is out of contact with liquid being heated and thereby is capable of heating to temperatures capable of damaging the materials of the heater apparatus. After the operating conditions that caused the alarm condition previously described are corrected, the heater 13 or 14 may again be powered by pressing the ON button 59 which turns on transistor 61 that re-energizes relay 58 and recycles the power-on reset circuit including amplifier 63 and latch 51. Suitable modifications or switched reconfigurations of the described circuitry may be made to detect the resistance of the heater 13 or 14 only after an extended period of no applied power to assure that the heater conductor is in substantially thermal equilibrium with the fluid being heated. Then, the sensed resistance of the heater 13, 14 provides an indication of the temperature of the heater fluid rather than of the heater 13, 14 for controlling a conventional temperature readout, or for further controlling power thereafter applied to the heater 13, 14. Actual thermal equilibrium may be predicted promptly, rather than being achieved only after long delay, by sensing the heater resistance at successive brief intervals to predict the asymtotic final value (i.e. the equilibrium temperature) from the exponential variations of resistance in successive intervals. Of course, other conventional power controller circuits, for example, including self-balancing bridge circuitry with the heater 13, 14 connected in one circuit arm of the bridge, may also be used to assure fail safe operation of the connected heater apparatus during changing operating conditions. Alternatively, conventional control circuitry, for example, as described in the aforecited U.S. Patent may be used to control applied electrical power in response to the electrical indication provided by thermistor 22 or 29, or may be modified in conventional manner to operate on the sensed resistance of the heater rather than on the thermistor signals, as disclosed therein.

Figure 4:
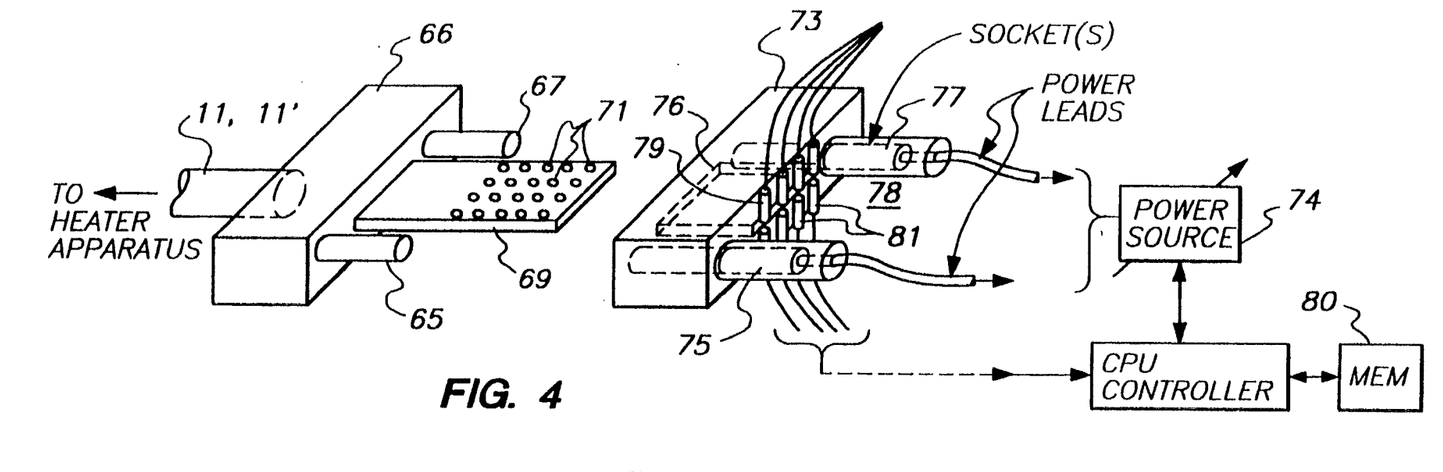
FIG. 4 is a perspective view of one embodiment of connector apparatus for encoding information about the heater apparatus and for detecting the encoded information to affect operation of the controller in powering the heater apparatus of FIGS. 1 or 2.

In accordance with another embodiment of the present invention, a coded connector or plug, as illustrated in FIG. 4, is attached to the heater apparatus for retaining coded information about the heater apparatus that can be detected by a power controller which is capable of being programmed to operate in accordance with the coded information contained in the plug. In the illustrated embodiment, the elongated tab 11 or connecting cable 11' of the heater apparatus terminates in an attached plug 66 having a pair of conductors 65, 67 for the heater 13 or 14, and having two or more electrical contacts, and having a tab or 'tongue' 69 attached to the plug 66 containing coded information. Specifically, the tab 69 includes a flat region capable of retaining coded information, for example, as bar codes or as rows and columns of holes 71 at selected locations that can be sensed by a mating receptacle 73 as the tab 69 and conductors 65, 67 are inserted into the receptacle. Several rows of 4-bit code may be assembled on the tab, as shown, or more complex 8-bit coding may be compacted onto the tab of any convenient length. Thus, the heater apparatus may be mass produced with low tolerances for resistance values of the heater 13 or 14 that is formed as a wire, or deposited film, or etched foil, or the like, and that is then tested at, say, room temperature to determine its initial test-value resistance which is then encoded into the tab 69 via suitable bar codes or patterns of holes 71, or the like. In addition, the temperature coefficient of resistance of the heater may be coded into the tab 69 along with data regarding other operating parameters such as maximum allowable operating temperature, nominal allowable current and voltage values to power the heater, and the like. Thus, according to the method of the present invention, an inexpensive electrical heater for medical applications of any description (e.g. immersible heaters, hemostatic thermal scalpels, and the like) may be mass produced to low-level tolerances, and then tested accurately to establish the requisite coded information to be encoded on tab 69 regarding its electrical and operational parameters.

Then, in operation, the plug 66 is inserted into the receptacle to establish connection between the respective sets of conductors 65–75 and 67–77 in the plug 66 and receptacle 73. In the process of establishing the connections, the tab 69 enters the slot or receiving port 76 of the receptacle in alignment with rows (or columns) of optical sensors 78. These sensors include a light source or sources 79 and individual optical detectors 81 of conventional design which sense light through apertures 71 (or reflections from bar codes) as the tab 69 is inserted through the slot or receiving port 76. The coded segment of the tab 69 is preferably positioned sufficiently forward of the conductors to assure detection of the code prior to connection of the conductors. In additions, the plug 66 and receptacle may be made asymmetrical, for example, by off-setting the tab from central orientation, or by dissimilar shapes of conductors 65, 67, or the like, to assure only one orientation of the plug 66 within the receptacle 73. The detectors 81 are connected to a microprocessor-controlled power source 74 of conventional design that can sense the coded information from detectors 81 to set the operating parameters within which the connected heater will be powered and operated. Thus, the power source 74 may automatically accomodate a heater for operation at not more than 22° C. at nominally 1 ampere and 20 volts, and a different heater having a different thermal coefficient of resistance for a different application may be operable up to 65° C. at nominally 3 amperes and 35 volts using the same microprocessor-controlled power source 74. In addition, time of operation, and numbers of operations, and other such operational data of a designated heater may all be encoded in the tab 69 using serial number or model number designation which are then compared with look-up table data in storage in the memory 80 to assure correct automatic setting of operating parameters for any resistance unit connected to the power source 74.

Figure 5:
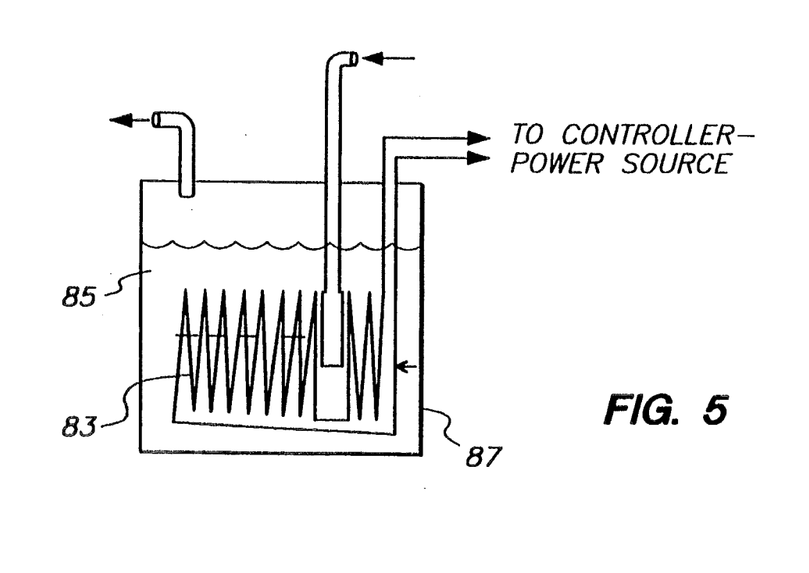
FIG. 5 is a sectional view of one embodiment of a gas heating unit according to the present invention.

Referring now to FIG. 5, there is shown a sectional view of a water-bath type of heat exchanger including a foil-type heater element 83, as previously described, disposed within a volume of water 85 that is confined within a vessel 87. A gas inlet tube 89 (e.g., for $CO_2$ or air) terminates below the surface level of the water and diffuses inlet gas under pressure through the water 85 which has been warmed by the heater element 83 to provide warmed, moistened gas at the outlet 91 that exhausts gas above the surface of the water 85. Of course, the vessel 87 may be formed as a sealed, flexible container, for example, of polyvinyl chloride that may be disposed of after a single use.

Figure 6:
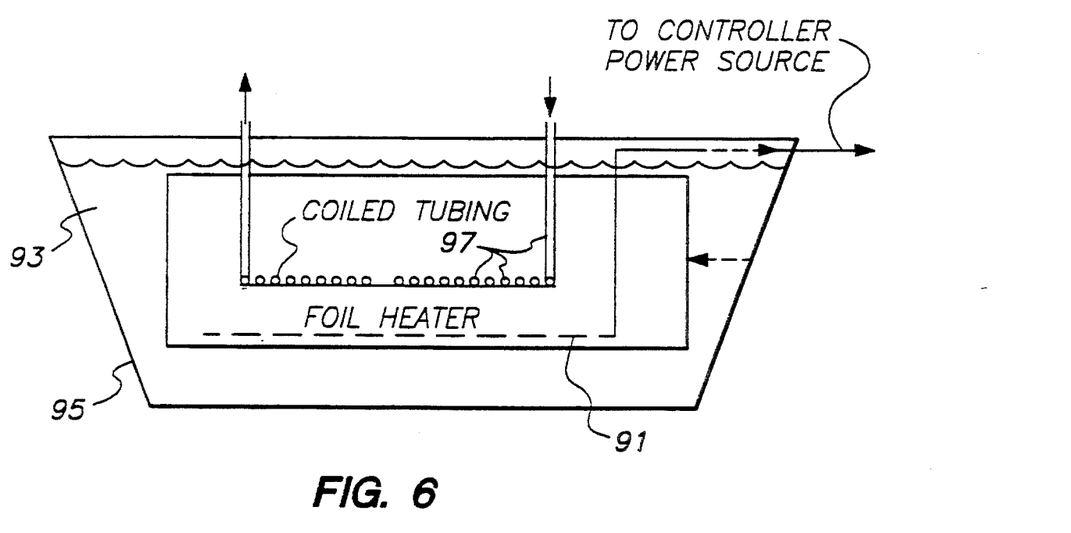
FIG. 6 is a sectional view of one embodiment of a liquid heating unit according to the present invention.

Similarly, with reference to FIG. 6, there is shown a cross sectional view of a water-bath type of heat exchanger including a foil-type heater 91, as previously described, disposed within a volume of water 93 that is confined within a vessel 95 to surround a coil of tubing 97 that carries a gas or liquid therethrough which is to be warmed. Of course, the vessel 95 may be formed as a sealed, flexible container, for example, of polyvinyl chloride to form a heating unit that may be disposed of after a single use.

Figure 7:
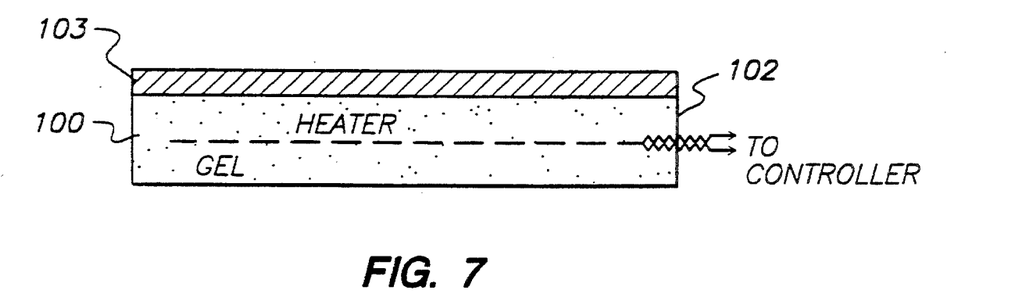
FIG. 7 is a sectional view of a heater packet for applying heat, for example, to a selected region of a patient.

Referring now to FIG. 7, there is shown a sectional view of a heater packet including a foil-type heater, as illustrated in FIG. 1, immersed in a thermally-conductive gel or liquid 100 such as silicone, or bentonite or starch in water, or the like, encapsulated within a flexible container 102, for example, of polyvinyl chloride to form a convenient, controllable heat pack that may be powered by the controller circuitry of FIG. 3(a) and then disposes of after a single use. The gel or liquid 100 serves as a thermal conductor that promotes more uniform heating over the surface of the packet, and a foam-type insulating layer 103 may be provided on one face of the packet to moderate the heat available for transfer from the packet to a patient in a topical heating application, or to protect attending personnel from contact with surfaces of elevated temperature while handling the packet.

Figure 8A:
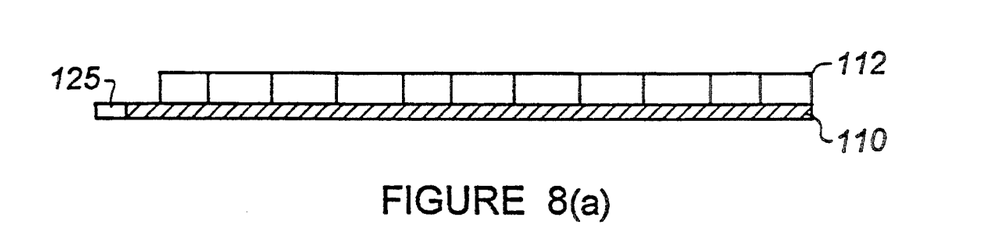
FIGS. 8(a) and 8(b) are sectional views, respectively, of single-sided and double-sided heater cassettes according to another embodiment of the present invention.
Figure 8B:
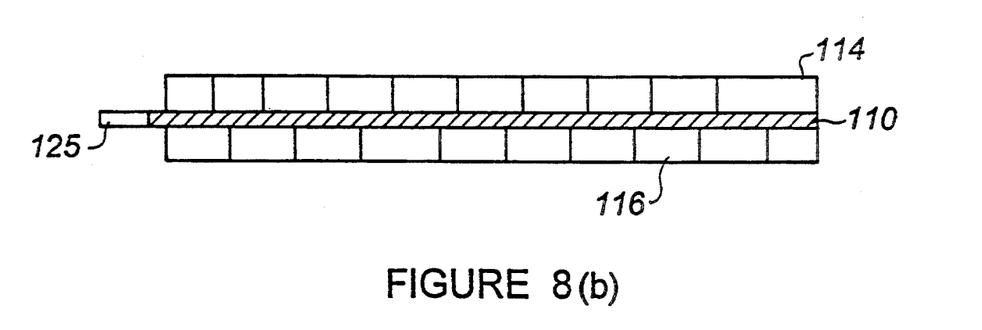
Figure 9:
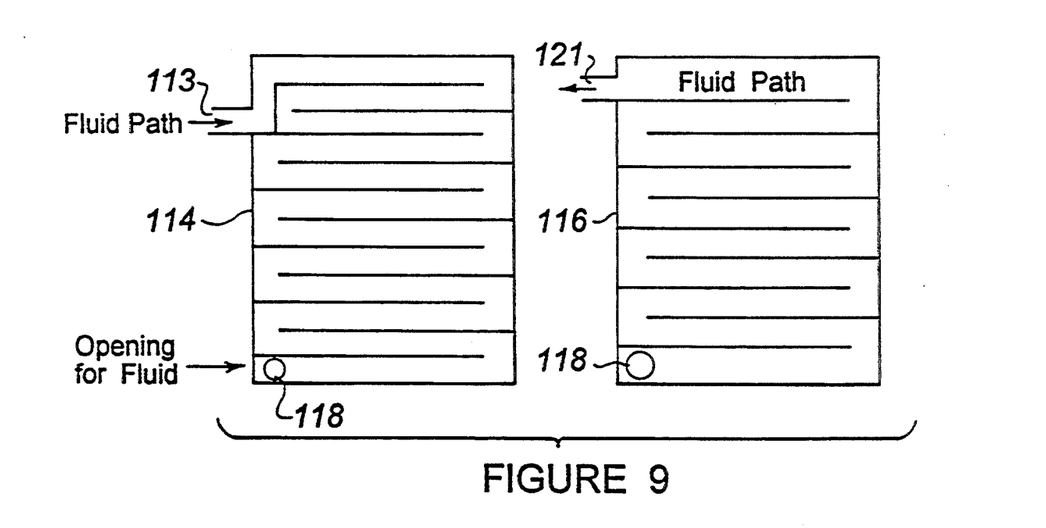
FIG. 9 is a plan view of unfolded upper and lower flow channels of a double-sided heater cassette according to the embodiment of FIGS. 8(a) and 8(b)
Figure 10:
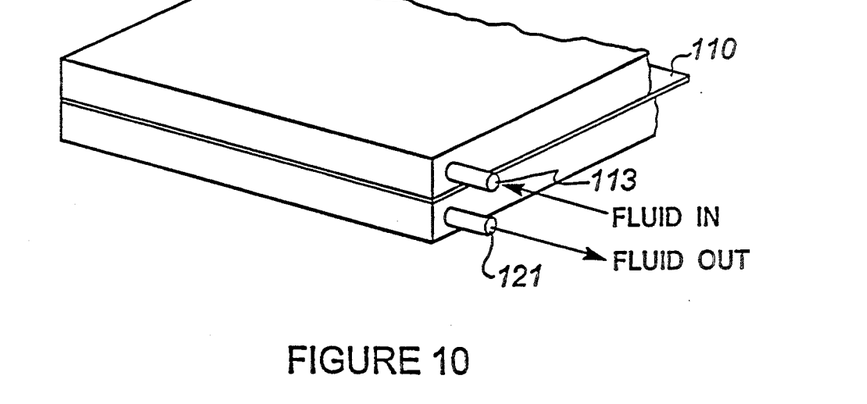
FIG. 10 is a partial perspective view of the heater cassette according to the illustrated embodiment of FIGS. 8(a) and 8(b)

Referring now to FIGS. 8(a) and 8(b), there are shown sectional views, respectively, of single-sided and double-sided heater cassettes in accordance with other embodiments of the present invention. In these embodiments, a foil-type heater 110 of the type previously described is disposed adjacent or between fluid-directing flow controllers 112, 114, 116 that are sealed about the foil-type heater 110 to form a serpentine or labyrinth-like pattern, as shown in FIG. 9, of fluid flow over one or more surfaces of the heater 110. As illustrated in FIG. 9, the fluid path may enter the upper segment 114 of the flow controllers and pass in serpentine manner over the surface of the adjacent heater 110 to an opening 118 that may be an outlet for a single-sided cassette, as in FIG. 8(a), or that may be an internal passage to the lower segment 116 of the flow controllers that continues the channelling of fluid flow in serpentine manner to the outler 121 fluid thus directed over the surface, or surfaces, of an adjacent heater 110 for more efficient transfer of heat therefrom to the fluid flowing through the flow controller 112, 114, 116 which may be formed of biologically-inert plastic material that provides thermal and electrical insulation in a self-contained fluid heater which is ready for connection, for example, into an intravenous liquid infusion set for delivering warmed liquid medicaments, or blood, or the like, to a patient.

Figure 11:
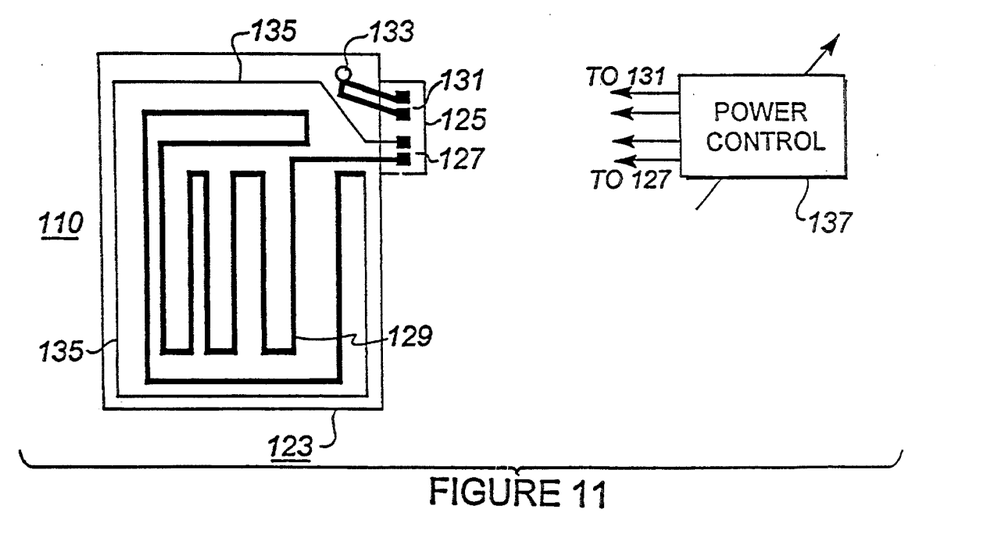
FIG. 11 is a plan view of a typical heater foil for disposition between upper and lower flow channels in the illustrated embodiment FIGS. 8(a) and 8(b).

Referring now to FIG. 11, there is shown a plan view of a foil-type heater 110 that is encapsulated between upper and lower sections of flow controllers 112, 114, 116 of a fluid-heating cassette. Specifically, the heater includes a supporting layer 123 of biocompatible, electrically insulating material such as polyvinyl chloride or silicone rubber, or the like, generally shaped in the outline of the perimeter of the upper and lower sections of the associated flow controllers 112, 114, 116, with an integral connector tab 125 that supports contacts 127 for receiving electrical signal to power the heater element 129, and contacts 131 for connection to thermal sensor 133. The heater element 129 may be covered with a biologically-inert layer and the length of the heater (from top to bottom edge), or a remote corner of the support layer 133 may be dimensioned to avoid interfering with the openings and passage 118 formed between upper and lower flow controllers 112, 114, 116.

In the embodiment, a foil-type distributed fusing link 135 may be disposed substantially about the perimeter of the support layer 123 to connect an end of the heater element 129 to one of the power contacts 127. In this way, absence of sufficient fluid flowing in contact with the heater (or in contact with the inert layer over the heater) to enable the heater to dissipate its heat will enable the fusing line 135 to burn out at any location therealong where 'hot spots' of undissipated heat may develop. This feature of the present invention safely obviates the potential fire hazard and thermal decomposition of polymeric materials in the support layer 123 and layer over the heater element 129 and flow controllers 112, 112, 116 that might otherwise occur due to excessive elevated temperatures of the heater element 129 operating in an environment of insufficient fluid flowing in contact with the heater. The heater element 129 and fusing link 135 may be formed of sputtered aluminum or etched form aluminum foil, or the like, at different cross sectional dimensions (e.g., different trace widths for common trace thicknesses) to assure higher probability of failure or burn out at elevated temperatures in the fusing link 135 than in the heater element 129.

In operation, the heater element 129 is connected via contacts 127 to a source 137 of electrical signal, for example from a power controller as described with reference to FIG. 3(a), to receive electrical within a selected range of voltages and currents to generate heat in the element 129. In addition, the thermal sensor 133 and may be disposed near the fluid outlet 121 of the cassette and may be connected via contacts 131 to such a power controller 137 to control the current voltage that is supplied thereby to the heater element 129 in order to control the temperature of fluid flowing out of the outlet 121 of the cassette. Circuitry of the power controller 137 may perform a determination of initial resistance of the heater element 129 and fusing link 135, for example, in the manner as previously described with reference to FIG. 3(a), to determine whether such initial resistance is within an acceptable range of tolerances to be services by the power controller 137, and to determine such other operating parameters as maximum allowable resistance change compared with the initial resistance (as determined during subsequent resistance-measuring intervals), and the like. In this way, multiple, independent fail-safe mechanisms are provided according to the present invention to assure proper operation within prescribed operating limits without operator surveillance or intervention following hook-up and initial power of the cassette. These safety mechanisms include resistance-measurement of the heater element 129, and/or sensing of the signal from thermo sensor 133 to control applied electrical power, and fused interruption of electrical power supplied to the heater element 129 in the event of excessive temperatures for any operating reason.

Therefore, the heating apparatus of the present invention permits inexpensive heaters having wide-ranging electrical parameters to be operated in fail-safe manner to avoid thermal runaway and damage under changing operating conditions. In addition, different electrical and operating parameters for heaters configured for different applications may be automatically sensed via encoded plugs and properly powered under tightly regulated conditions in accordance with the coded parameters.

I claim:

1. Heating apparatus for medical applications comprising:
    a first layer of electrically-insulating biologically-inert material for supporting a heater element thereon;
    a heater element of electrically-conductive material disposed on a selected region of the first layer;
    a second layer of electrically-insulating, biologically-inert material disposed over the heater element and sealed to the first layer for forming an immersible structure; and
    a housing of biologically inert material having an inlet and an outlet and being disposed on one of the first and second layers for directing the flow of a fluid to be heated by the heater element within a selected pattern in contact with the one of the first and second layers from the inlet to the outlet.

2. Heating apparatus according to claim 1 comprising:
    a pair of housings of biologically-inert material each having an inlet and an outlet, the housings being disposed on the first and second layers for directing the flow of a fluid within a selected pattern in contact with the respective first and second layers from an inlet of one of the pair of housings to the outlet thereof and then to the inlet of the other of the pair of housings, to the outlet thereof.

3. Heating apparatus according to claim 1 comprising fuse means disposed on the first layer at a location thereon disposed near at least one of said inlet and outlet.

4. Heating apparatus according to claim 1 wherein the selected pattern includes a continuous serpentine course between said inlet and outlet.

* * * * *